United States Patent [19]
van den Ouweland et al.

[11] 4,080,367
[45] Mar. 21, 1978

[54] FLAVORING SUBSTANCES

[75] Inventors: Godefridus Antonius Maria van den Ouweland; Hendricus Gerardus Peer, both of Zevenaar, Netherlands

[73] Assignee: Lever Brothers Company, New York, N.Y.

[21] Appl. No.: 745,311

[22] Filed: Nov. 26, 1976

Related U.S. Application Data

[62] Division of Ser. No. 838,053, Jun. 27, 1969, Pat. No. 4,020,170.

[30] Foreign Application Priority Data

Jul. 1, 1968 United Kingdom ............... 31378/68

[51] Int. Cl.$^2$ .................. C07D 307/20; C07D 307/32
[52] U.S. Cl. ................................................. 260/347.2
[58] Field of Search ..................... 260/347.2; 426/535

[56] References Cited
FOREIGN PATENT DOCUMENTS 946,441  7/1956  Germany.

*Primary Examiner*—Richard L. Raymond
*Attorney, Agent, or Firm*—Melvin H. Kurtz

[57] ABSTRACT

Novel sulphur containing food flavor substances are provided containing an oxygen or sulphur atom in a five or six membered ring structure, one alkyl or hydroxy alkyl substituent at at least either of the carbon atoms adjacent to the hetero atom and having at least one sulphur or oxygen atom attached to another carbon atom of the ring structure.

3 Claims, No Drawings

FLAVORING SUBSTANCES

This is a division, of application Ser. No. 838,053, filed June 27, 1969, now U.S. Pat. No. 4,020,170.

The invention relates to food flavouring substances, their preparation and their use in the flavouring of foodstuffs. In particular the invention is concerned with substances capable of imparting a savoury flavour, for example a flavour resembling that of roast, fried or boiled meat, to foodstuffs. The invention furthermore relates to foodstuffs to which such a flavour has been imparted or in which such a flavour is enhanced by judicial incorporation of these flavouring substances.

Flavouring is understood to be the incorporation of compounds having flavouring characteristics per se as well as the incorporation of precursor compounds which do not themselves posses flavouring characteristics but which during the preparation of the foodstuff release or are converted into products having flavouring characteristics.

It has not been found that certain novel sulphur containing heterocyclic compounds possess flavour characteristics remarkably similar to that of prepared meat or meat products and which are valuable as food flavouring agents. The invention provides novel sulphur containing heterocyclic compounds of the general formula

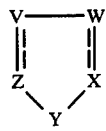

in which
—Y— represents —O— or —S—,
===Z— represents —CHR$^1$— or =CR$^1$,
===V— and ===W— represent
—C—, —C—, —CH$_2$—, =CH—,
‖    ‖
O    S
—CHSH—, ===CSH— or ===COH—, ===X — represents =CR$^2$ —, —CHR$^2$ —, — CH$_2$ — CHR$^2$ — = CH — CHR$^2$, =CR$^2$ — CH$_2$ — or — CR = CH—, and R$^1$ and R$^2$ represent a hydrogen atom, an alkyl or hydroxylalkyl group containing 1-4 carbon atoms, with the provisions that the total number of carbon atoms of groups R$^1$ and R$^2$ together is at least 1 but below 9, and at least one of the groups —Y—, ===V— and ===W— comprises a sulphur atom.

As is apparent from the above, the groups ===V— and ===W— may represent groups such as

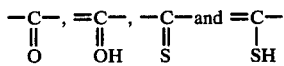

indicating the occurrence of keto-enol tautomerism in the compounds involved so that the actual compounds will often occur in more than one structure.

In an embodiment of the invention substances are provided of a general formula in which each of the groups ===V— and ===W— comprises an oxygen atom. These compounds, in which — X — represents sulphur, possess per se relatively weak flavouring properties but may be converted into compounds having interesting flavouring properties, by reacting with hydrogen sulphide or to some extent when reacting with water.

In another embodiment of the invention compounds of the above general structure are provided with the provision that at least one of the groups ===V— or ===W— comprises a sulphur atom and, in case that — Y — also represents a sulphur atom, that the structure contains less than 2 double bonds. In view of the occurrence of various tautomeric structures in these compounds the number of double bonds to be counted includes carbon to carbon, carbon to oxygen and carbon to sulphur double bonds.

Food flavouring substances having characteristics similar to that of roast or fried meat are further obtained in case the group ===V— comprises a sulphur atom, in particular in case it represents

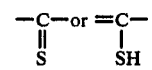

in which case group ===X— should preferably represent =CR$^2$— or — CHR$^2$—.

Also variation in group ===W— has an appreciable effect on the flavouring characteristics. So it has been found that in case at least one of the groups, ===V— or ===W— comprises a sulphur atom and the other above-mentioned provisions are complied with, and furthermore in case ===W— represents —CH$^2$—, the compounds show a pronounced roast or fried meat flavour. However, if ===W— represents

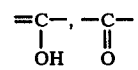

or = CH —, the flavouring characteristics may range from roast or fried meat to fried onion.

The invention provides in particular flavouring substances of the following general formulae in which — Y — represents an oxygen or a sulphur atom and R$^1$ and R$^2$ represent a hydrogen, an alkyl or hydroxylalkyl group containing together from 1–9 carbon atoms:

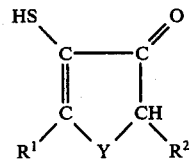

Examples of compounds of this class are:
4-mercapto-5-methyl-2,3-dihydrothiophene-3-one.
4-mercapto-5-methyl-2,3-dihydrofuran-3-one.
4-mercapto-2,5-dimethyl-2,3-dihydrothiophene-3-one.
4-mercapto-5-ethyl-2,3-dihydrofuran-3-one.
4-mercapto-2-ethyl-5-methyl-2,3-dihydrothiophene-3-one.

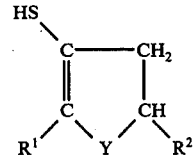

Examples of compounds of this class are:
3-mercapto-2-methyl-4,5-dihydrofuran
3-mercapto-5-methyl-4,5-dihydrofuran
3-mercapto-2-methyl-4,5-dihydrothiophene
3-mercapto-5-methyl-4,5-dihydrothiophene
3-mercapto-2,5-dimethyl-4,5-dihydrofuran
3-mercapto-2,5-dimethyl-4,5-dihydrothiophene
3-mercapto-5-ethyl-4,5-dihydrofuran
3-mercapto-2-ethyl-5-methyl-4,5-dihydrothiophene.

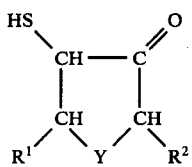

Examples of compounds of this class are:
4-mercapto-5-methyl-tetrahydrofuran-3-one
4-mercapto-5-methyl-tetrahydrothiophene-3-one
4-mercapto-2,5-dimethyl-tetrahydrofuran-3-one
4-mercapto-2-ethyl-tetrahydrothiophene-3-one
4-mercapto-2-ethyl-5-methyl-tetrahydrofuran-3-one.

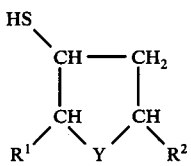

Examples of compounds of this class are:
3-mercapto-2-methyl-tetrahydrofuran (cis and trans)
3-mercapto-5-methyl-tetrahydrofuran (cis and trans)
3-mercapto-2,5-dimethyl-tetrahydrofuran
3-mercapto-5-methyl-tetrahydrothiophene (cis and trans)
3-mercapto-2-methyl-tetrahydrothiophene (cis and trans)
3-mercapto-2,5-dimethyl-tetrahydrothiophene
3-mercapto-5-ethyl-tetrahydrofuran (cis and trans)
3-mercapto-2-ethyl-5-methyl-tetrahydrothiophene.

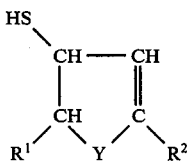

Examples of compounds of this class are:
3-mercapto-2-methyl-2,3-dihydrothiophene
3-mercapto-5-methyl-2,3-dihydrothiophene
3-mercapto-2,5-dimethyl-2,3-dihydrofuran
3-mercapto-2-methyl-2,3-dihydrofuran
3-mercapto-5-methyl-2,3-dihydrofuran
3-mercapto-5-ethyl-2,3-dihydrothiophene
3-mercapto-2-ethyl-5-methyl-2,3-dihydrofuran.

The above formulae and systematic names have been represented in the form of the most probable tautomeric structure.

The flavouring characteristics of compounds satisfying the above five general formulae and their tautomers were found to be particularly interesting in case $R^1$ and $R^2$ represnt a hydrogen atom, a methyl group or a hydroxy methyl group.

Flavouring compounds mentioned above can be prepared by various methods, as e.g.

I. A diketo dithioester of the general formula

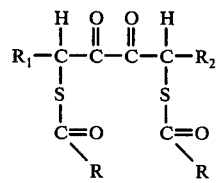

in which R represents an alkyl group, preferably $C_2 - C_4$, can be cyclized into a thiophene under the influence of protons in an aqueous medium, and the thiphenone isolated II. A diketo dithioester, e.g. a ditosylate of the formula

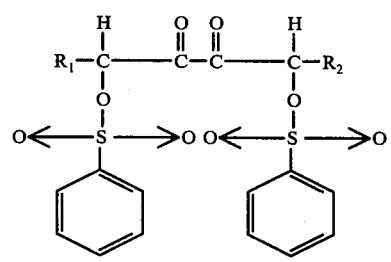

can be cyclized with disodium sulphide in an aqueous medium, and the thiophenone isolated.

III. Cyclic compounds with a sulphur atom attacked to a saturated carbon atom are synthesized by reacting the corresponding halogeno compound with potassium thiolacetate in acetone or dimethylformamide and subsequent hydrolysation with sodium methoxide in methanol.

IV. Cyclic compounds with a sulphur atom attacked to a saturated carbon atom with less than two double bonds in the ring structure are synthesized by the following reaction path: the corresponding ketone is reduced by Li AlH$_4$, converted into their p-toluene sulfonic esters and subsequently into the thioacetate. Hydrolysation then yielded the sulphur compound.

V. Cyclic compounds with a sulphur atom attacked to an unsaturated carbon atom are synthesized by the reaction of the corresponding ketone with hydrogen sulphide in ethanol saturated with hydrogenchloride and ether at $-80°$ C.

VI. Thioketones or compounds with a sulphur atom attacked to an unsaturated carbon atom are obtained by reacting the corresponding ketone with phosphor pentasulphide in toluene at reflux temperature.

A preferred method for preparing mixtures in which several flavouring compounds according to the invention occur is reacting a heterocyclic compound of the general structure:

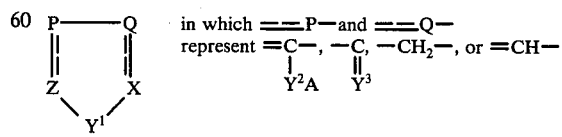

in which ═P— and ═Q— represent ═C—, —C, —CH$_2$—, or ═CH—
$\phantom{represent ═C—, —}\overset{|}{Y^2}A \phantom{,}\overset{\|}{Y^3}$ with the provision that not more than one may represent a —CH$_2$—group, or ═ CH —. A represents hydrogen or an organic acid radical containing 1 - 7 carbon atoms, $Y^1$, $Y^2$ and $Y^3$ represent oxygen or sulphur atoms of which not more than one represents a sulphur atom,

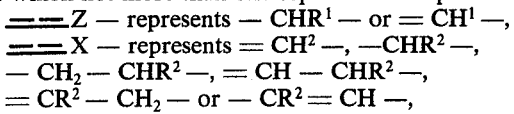

and $R_1$ and $R^2$ represent a hydrogen atom or alkyl or hydroxyalkyl group containing 1 – 4 carbon atoms, with the provision that the total number of carbon atoms is at least 1 but below 9, with hydrogen sulphide or a hydrogen sulphide liberating compound in the presence of water.

It is particularly preferred to use such compounds as starting material for the reaction with hydrogen sulphide in which ====P —,

or Q represents

In a preferred embodiment of this preparative method ====Z — represents — $CHR^1$ — or = $CR^1$ —

In a further embodiment $R^1$ and $R^2$ represent a hydrogen atom, a methyl group or hydroxymethyl group, and the groups $Y^1$, $Y^2$ and $Y^3$ may represent oxygen atoms.

Starting materials satisfying the above requirements constitute furanone compounds which may be reacted with hydrogen sulphide such as:

4-hydroxy-5-methyl-2,3-dihydrofuran-3-one
4-hydroxy-2,5-dimethyl-2,3-dihydrofuran-3-one
4-hydroxy-2-methyl-5-ethyl-2,3-dihydrofuran-3-one
4-hydroxy-5-methyl-2-ethyl-2,3-dihydrofuran-3-one
4-hydroxy-2,5-diethyl-2,3-dihydrofuran-3-one
4-hydroxy-2-hydroxymethyl-5-methyl-2,3-dihydrofuran-3-one
4-acetoxy-5-methyl-2,3-dihydrofuran-3-one
4-methoxy-2,5-dimethyl-2,3-dihydrofuran-3-one Of these furanones, the first three named examples are the most preferred. The alkyl substituted furanones which are used according to the present invention can be prepared by heating and reacting a diketo diester of the general formula:

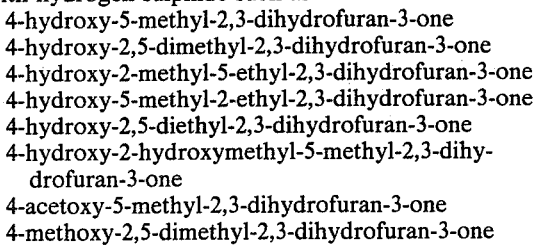

in which $R_1^1$ and $R_2^2$ represent a hydrogen atom or an alkyl radical containing 1 or 2 carbon atoms, with the provision that the number of carbon atoms of $R_1^1$ and $R_2^2$ together is at least one and $A_1^1$ and $A_2^2$ represent acid radicals. The acid radicals may be derived from carboxylic acids, especially from lower aliphatic carboxylic acids. Preferred ester groups are those derived from acetic and propionic acid.

The reaction is carried out in an aqueous acidic medium which contains at least 50 percent by volume, preferably at least 75 percent of water, the remainder being a water-miscible polar solvent as, for example a lower aliphatic alcohol such as methanol and ethanol.

The acidic compound available in the aqueous acidic medium may comprise an inorganic acid, a carboxylic acid, or, for example, an organic sulphonic acid. Suitable acids include hydrobromic or hydrochloric acid, sulphuric acid, phosphoric acid, formic acid, acetic acid, propionic acid, -p-toluene sulphonic acid and the like. Polycarboxylic acids and hydrocarboxylic acids are less suitable. The use of strong acids, showing a pH value below 5 or rather below 4, is particularly preferred.

The amount of acid in the aqueous medium is not particularly critical and may vary widely. Good results have been obtained with amounts of 0.1–5 equivalents of acid per liter medium. Also the concentration of the diketo diester in the aqueous medium may vary widely. Generally, less than 200g of diketo diester are dissolved per liter of medium. For practical reasons, in particular to reduce the volume of the reaction mixture, the use of too dilute solutions is avoided. A practical range is from 10–100g of diketo diester per liter medium.

The reaction temperature and time of reaction are related. For convenient reaction periods in the range of 0.5–10, preferably from 1–5 hours, it is preferred to conduct the reaction at temperatures above 75° C, preferably at boiling temperature at atmospheric pressure. It is however possible to obtain a satisfactory conversion at lower temperatures, for example of about 50° C, provided the reaction period is suitably adjusted to at least 20 hours.

After termination of the reaction the aqueous reaction mixture is allowed to cool and the desired furanone derivative is isolated in a conventional way. This could be done, for example, by extraction with ether, drying of the etheral solution and evaporation of the solvent. Undesired polymeric contaminants are removed by distillation of the product under diminished pressure.

Esterification or etherification of the hydroxyl group in the 4-position may be achieved by conventional methods.

The diketo diester starting materials for the process according to the invention can be prepared in various ways. A convenient method is via acetylenic compounds. Step 1 - Preparation of an alkyne diol.

Acetylene was coupled with two moles of aldehyde using two moles of a Grignard compound. This method is described in Bull. Soc. Chim. - France 425 (1956). Alternatively a 1-alkyne-3-ol could be coupled with formaldehyde as described in Annalen 596 525 (1955) or by coupling a 1-alkyne-3-ol and other aldehydes or ketones (as described in Bull Soc. Chim. supra). Step 2 - Esterification of the alkyne diol.

The diacetates were conveniently prepared by reacting with acetic anhydride in the presence of e.g. pyridine or sodium acetate. Step 3 - Oxidation of the alkyne diester The alkyne diester was oxidized with dilute aqueous potassium permanganate at a low temperature yielding the diketo diester. This method has been described in Bull. Soc. Chim. (France) 769 (1949).

Preferred examples of the pyrones which may be reacted with hydrogen sulphide according to the invention are:

3-hydroxy-2-methyl-1,4-pyrone (maltol)
3-hydroxy-2-ethyl-1,4-pyrone (ethyl maltol)

The sulphur containing compound with which the furanone or pyrone is reacted is hydrogen sulphide, in the form of a gas, liquid or solution, or an organic or inorganic compound which is capable of liberating hydrogen sulphide, either in gaseous or nacent form, under the reaction conditions.

Suitable examples of organic sulphur-containing compounds are cysteine, or a peptide containing cysteine such as glutathione, cystine mercaptoacetamide, thioacetamide or salts, for example potassium or sodium salts, hydrochlorides, esters or other simple derivatives of these sulphur-containing compounds.

Suitable examples of inorganic sulphur-containing compounds are sulphides or hydrosulphides of alkali metals, alkaline earth metals or ammonia, such as sodium sulphide, potassium sulphide, ammonium sulphide, calcium sulphide or the corresponding hydrosulphides. Also, other inorganic metallic sulphides, for example ferrous sulphide, may be used.

The reaction mixture comprising at least one ketone and hydrogen sulphide or a sulphur-containing compound as herein defined which react to form the flavour substances according to the invention, may optionally also contain other ingredients which improve or enhance the character of the flavour which subsequently is produced. These optional ingredients may be added before, during or after the ketone and hydrogen sulphide or sulphur-containing compound react.

Thus it is possible to include in the reaction mixture amino acids, the preferred amino acids being one or more of the following: arginine, glutamic acid, proline, glycine, $\alpha$-alanine, $\beta$-alanine, threonine, lysine, leucine, iso-leucine, serine, valine, histidine, cysteine and cystine or a salt thereof. Cysteine and cystine may of course serve in the reaction as sulphur-containing compounds according to the invention.

It is also possible to include in the reaction mixture as an optional ingredient a monosaccharide or a carbohydrate which is capable of being hydrolysed to a monosaccharide under the conditions of the reaction. The most suitable monosaccharides are hexoses, such as glucose, and pentoses, such as ribose, xylose, rhamnose and arabinose.

It is also possible to conduct the reaction in the presence of $C_{12}$–$C_{18}$ aliphatic fatty acid, for example, palmitic acid or oleic acid or a salt, ester or glyceride thereof.

The proportions of the ketone to hydrogen sulphide or sulphur-containing compound which are present in the reaction mixture may vary widely. Thus it is possible to use proportions on a weight basis of from 1 part ketone and 50 parts hydrogen sulphide or sulphur-containing compound to 50 parts ketone and 1 part hydrogen sulphide or sulphur-containing compound. Preferred weight proportions are between 1 part ketone and 10 parts hydrogen sulphide or sulphur-containing compound to 10 parts ketone and 1 part hydrogen sulphide or sulphur-containing compound.

Where the reaction conditions are such that excess hydrogen sulphide remains after the reaction is complete, it is advisable to allow the reactants to stand, or to apply ventilation or other means to remove the excess hydrogen sulphide, otherwise the flavour substance may be objectionable due to residual hydrogen sulphide.

The reaction should be conducted under conditions in which at least a trace amount of water is present in the reaction mixture; suitably the amount of water present should be at least equal by weight to the amount of hydrogen sulphide or the sulphur-containing compound. It is however preferred for reasons of convenience that the weight of water should be at least equal to that of the reactants, so that intimate mixing of the ingredients is thereby facilitated. In general it is not necessary that the weight of water present should exceed 100 times that of the reactants, primarily to facilitate subsequent concentration of the flavouring substances which are the products of the reaction. It is also possible to conduct the reaction where the water is bound in the form of water of crystallisation. As an example, sodium sulphide nonahydrate may be employed in the reaction to act both as a sulphur containing compound and as a source of water.

The rate at which the ketone and hydrogen sulphide or sulphur-containing compound react is dependent on the temperature of the reaction mixture, higher temperatures in general resulting in a faster rate of reaction. However, we have found that it is possible to obtain the flavour substances according to the invention by employing a reaction temperature of between 0° and 150° C, but for practical purposes it is preferred and is more convenient to employ a temperature in excess of 60° C, and most preferably between about 90° and 110° C. This is particularly applicable when the reaction is carried out by refluxing at atmospheric pressure.

It is necessary to apply a pressure above that of atmospheric pressure when aqueous systems are heated at a temperature above the boiling point of the system at atmospheric pressure. It has also been found advantageous to employ superatomospheric pressures when one of the reactants is a gas, for example when gaseous hydrogen sulphide is employed.

When the reaction is conducted in the presence of more than a trace amount of water, the pH of the reaction mixture may vary over a wide range of values. The reaction thus may be conducted at pH values ranging from 2 to 10, but values between 4 and 7 are preferred.

The duration of the reaction may vary considerably and is, of course, dependent on other parameters which control the rate of reaction. We have, for example, found that the flavour substances are produced within a few minutes of commencing the reaction and continue to build up in the reaction mixture for several days. As a general guide, we have found that for a reaction temperature of 100° C, a reasonable reaction time is from 1 minute to 15 hours, whereas at room temperature, the flavour composition may be produced in as little as 3 minutes to as long as 30 days. It is, however, preferred to restrict the reaction time to between 1 and 6 hours.

According to a preferred embodiment of the invention, a ketone and a sulphur-containing compound giving rise to hydrogen sulphide are reacted together in the presence of water by boiling or simmering under reflux at a temperature slightly in excess of 100° C for about 3 hours. The aqueous reaction mixture may subsequently be concentrated to a paste or dried to powder, care being taken to ensure that the loss of volatile components of the flavouring substance so produced is kept to a minimum.

The flavouring substances prepared according to the invention may thus be employed in liquid or semi-liquid form, for example as solutions, emulsions or pastes, or in dried form, for example as a powder. Drying of the reaction products may be accomplished for example by freeze-drying which has been found to be most suitable for optimum retention of flavour volatiles.

The flavouring substances thus prepared may be blended with a further quantity of a ketone as herein defined, which itself is capable of imparting a savoury taste to a foodstuff, or with one or more compounds from the following classes of substances:

I. Amino acids which may be obtained by hydrolysis, autolysis or fermentation or by combination of these from vegetable or animal proteins such as gluten, casein, soyabean protein and the like.

II. Nucleotides, such as adenosine-5′-monophosphate, guanosine-5′-monophosphate, inosine-5′-monophosphate, xanthosine-5′-monophosphate, uridine-5′-monophosphate, cytidine-5′-monophosphate, or their amides, desoxy derivatives or their salts. Combinations of nucleotides, for example guanosine-5′-monophosphate and inosine-5′-monophosphate are particularly suitable.

III. Carboxylic acids such as lactic acid, glycolic acid and γ-hydroxy butyric acid on one hand and dicarboxylic acids such as succinic acid and glutaric acid on the other hand, and especially mixtures of carboxylic acids in which succinic acid and lactic acid occur in weight ratios of 1:30 to 1:150.

IV. Pyrrolidone carboxylic acid or precursors thereof.

V. Peptides such as alanyl-alanine, alanyl-phenylalanine, alanyl-asparagine, carnosine and anserine.

VI. Sweetening substances, both artificial, such as saccharine and cyclamate, and natural, particularly mono- and disaccharides.

VII. Substances with the flavour of cooked or roast meat or of meat broth, (other than those which result from the reaction of a ketone with a sulphur-containing compound as hereinbefore defined), for example the reaction products of amino acids such as cysteine or cystine with reducing sugars, or ascorbic acid, or the reaction products of hyrogen sulphide with lower aliphatic aldehydes and ketones, such as propionaldehyde, crotonaldehyde, methional, mercapto-acetaldehyde.

VIII. Volatile sulphur compounds, such as hydrogen sulphides, mercaptans, disulphides and sulphides, such as dimethyl sulphide and diallyl sulphide.

IX. Guanidines, such as creatine and creatinine.

X. Salts such as sodium chloride, disodium hydrogen phosphate, monosodium dihydrogen phosphate or other alkali or ammonium phosphates and organic phosphates, such as phosphorus-containing amino acids.

XI. Nitrogen-containing compounds, such as ammonia, amines, urea, indole and skatole.

XII. Saturated or unsaturated carboxylic acids for example those containing from 2 to 12 carbon atoms in the molecule.

XIII. Saturated or unsaturated higher hydroxycarboxylic acids and γ and δ-lactones derived therefrom, such as deca- and dodeca-5-olide and 2,3-dimethyl-2,4-alkadiene-4-olides.

XIV. Lower saturated and unsaturated aldehydes, for example acetaldehyde, propion-aldehyde, iso-butyraldehyde and hepten-4-al.

XV. Lower saturated and unsaturated ketones, such as acetone, butanone and diacetyl.

XVI. Tricholomic acid and biotenic acid or their salts.

XVII. Aromatic and/or heterocyclic compounds, such as ortho amino-acetophenone, N-acetonyl pyrrole, iso-maltol, lenthionine, hypoxanthine, guanine, inosine and guanosine.

XVIII. Lower saturated and unsaturated alcohols, such as ethanol and octanol.

XIX. Colouring substances, such as curcuma and caramel.

XX. Thickening agents such as gelatin and starch.

XXI. Unsaturated $C_{12}$–$C_{18}$ aliphatic fatty acids and their glycerides or saturated glycerides.

The proportions of these optimally added substances used is dependent on the kind of flavour desired and also on the nature of the foodstuff to which they are added together with other ingredients, such as herbs and spices.

In addition to preparing flavouring substances for subsequent addition for foodstuffs, by reacting together a ketone and hydrogen sulphide as herein described, it is also possible to add the unreacted starting materials to the foodstuff so that the flavouring substances may subsequently develop in the foodstuff before consumption. Thus, for example, it is possible to add a ketone and a sulphur-containing compound capable of producing hydrogen sulphide to the ingredients of a soup which is subsequently canned and heat sterilised. A desirable roast meat-like flavour may thereby be developed within the soup after heat sterilisation in the sealed can.

The flavouring substances prepared according to the invention may otherwise be incorporated into foodstuffs, such as soups, sausage, reformed comminuted meat, simulated meat products, such as textured vegetable protein, and pastry products, in an amount sufficient to impart or enhance the desired flavour. Thus, flavouring amounts will vary according to the individual palate and according to the nature of the foodstuffs. As a general guide, the flavouring substances in amounts of from 1 ppm to 8,000 ppm have been incorporated in foodstuffs, these proportions being expressed on a weight basis.

As an illustration of suitable quantities of the flavouring substances that may be added to specified types of foodstuff, we have found that as little as 1 ppm to 10 ppm w/w is sufficient to impart a pleasant roast meat flavour to soups which are bland or otherwise lightly flavoured. On the other hand, when incorporating a similar roast meat flavour to already flavoured foodstuffs such as those based on vegetable protein, it may be necessary to incorporate larger amounts, for example from 600 to 8,000 ppm w/w of the flavouring substance in order to obtain a desirable flavour. In case a pure compound according to claim 1 is added to a foodstuff, from 0.05 to 50 ppm, preferably from 0.1 to 20 ppm (dry matter content) is added.

When the flavour substances prepared according to the invention are added to a foodstuff, it is believed that further reaction in situ in the foodstuff contributes to the development of the desired flavour characteristic. It would thus appear likely, for example, that sulphydryl groupings present in or derived from protein present in the foodstuff react further with the ketone derivatives in the flavour substance to produce compounds having improved flavour properties.

EXAMPLE A1

Preparation of 4-hydroxy-5-methyl-2,3-dihydrothiophene-3-one 140 g of commercially available 1-butyn-3-ol (boiling point 107° at atmospheric pressure) were treated in an aqueous solution with 200 g of a 30% formaldehyde solution in the presence of 10 g CuCl and refluxed for 50 hours. The resulting 156 g (70%) of 2-pentyn-1,4-diol (boiling point 115° C at 2.5 mm mercury) were isolated by evaporating off the water and distilling the residue.

50 g (0.5 m) of 2-pentyn-1,4-diol were dissolved in 250 ml of dry pyridine. The solution was stirred and cooled to −10° in an ice-salt mixture. With stirring, a cold solution of 286 g (1.5 m) of p-toluene sulfonyl chloride in 550 ml of dry dichloromethane was added dropwise, under exclusion of atmospheric moisture, from the dropping funnel, in such a manner that the temperature did not exceed −5° C. After completion of the addition (about 1.5 hours) stirring at 0° was continued for 5 hours, and water (30 ml) was added in portions at intervals of 5 min., with stirring and cooling, so that the temperature did not rise above 5°. The solution was then poured into 1000 ml of cold water. The mixture was extracted three times with dichloromethane; the combined extracts were successively washed with portions of ice-cold dilute sulfuric acid, water, sodium hydrogen carbonate solution and water. The dichloromethane solution was then dried with anhydrous sodium sulphate and evaporated to dryness, affording a sirup which crystallizes on standing. It was recrystallized from ethanol; yield 125 g = 61%; m.p. 80°-80.5° C.

A solution of the ditosylcompound (98 g = 0.24 m) and potassium thiolacetate (60 g = 0.527 m) in dimethylformamide (1.5 l) was stirred for 45 minutes at 40° C under nitrogen, then concentrated under reduced pressure and diluted with water (1 liter). The mixture was extracted five times with dichloromethane, the combined extracts were washed with water, dried with anhydrous sodium sulphate and evaporated to dryness. The residue was distilled through a short path column, affording 43.8 g = 84.5% of the dithioacetate; bp. 129°-130° at 1.6 mm mercury; $n_D^{20}$ = 1.5440. 20 g of the 1.4-dithioacetoxy-2-pentyn were then dissolved in 1000 ml of an alcohol-water mixture (90 : 10 by volume) and the solution was cooled to −25° C. A solution of 32 g potassium permanganate and 48 g magnesium sulphate hepta hydrate in 700 ml of water was slowly added in 2 hours whilst maintaining the temperature at −20° to −25° C.

The reaction mixture was stirred for another 2 hours at the same temperature, and 600 g of ice were then added. The reaction mixture was then extracted with cold chloroform. The light yellow coloured organic solution yielded after drying and evaporation of the solvent 13.5 g = 59% of a yellow oil (pentane-2,3-dione-1,4-dithioacetate).

10 g of the yellow oil thus obtained (pentane-2,3-dione-1,4-dithioacetate) were dissolved in 1500 ml of 0.5 N. aqueous hydrochloric acid and stirred for 1.5 hours at 95° C. After cooling the reaction mixture was extracted five times with chloroform, the combined extracts were washed with water, dried with anhydrous sodium sulphate and evaporated to dryness, affording a sirup which crystallized on standing. After recrystallization, from dichloromethane, white crystals of 4-hydroxy-5-methyl-2,3-dihydrothiophene-3-one were obtained; m.p. 152°-153° C; yield = 40%.

Infra-red absorption characteristics: maxima at 3200, 3000, 2930, 1665, 1615, 1600, 1400, 1368, 1360, 1305, 1190, 1133, 858, 848, 780, 640, 560 cm⁻¹. Nuclear magnetic resonance (NMR) date were:

| | δ | M | |
|---|---|---|---|
| | e, 1 2,24 | multiplet | 3H |
| | b : 3,60 | " | 2H |
| mass data: | m/e | i.% | m/e | i.% |
| i = intensity | 132 | 5 | 58 | 5 |
| | 131 | 6 | 57 | 6 |
| | 130 | 100 | 46 | 5 |
| | 71 | 6 | 45 | 7 |
| | 60 | 5 | 43 | 8 |

-continued

| 59 | 42 | 41 | 6 |

EXAMPLE A2

Preparation of 4-hydroxy-2,5-dimethyl-2,3-dihydrothiophene-3-one 34.2 g of 3-hexyne-2,5-diol (boiling point 103° at 2 mm mercury) were dissolved in 200 ml of dry pyridine. The solution was stirred and cooled to −10° C in an ice-salt bath. With stirring a cold solution of 172 g (0.9 mol) of p-toluene sulfonylchloride in 350 ml of dry dichloromethane was added dropwise (temp. <−5° C). After completion of the addition (2 hours), stirring at 0° was continued for 1 hour, and the solution was kept overnight at 0°, with the exclusion of moisture. After addition of water (20 ml) in portions, as described above, and stirring for 30 min., the product was isolated, as described above. Recrystallization from dichloromethane/pentane afforded the pure ditosylate with m.p. 118°-120°; yield = 101 g (80%).

70 g (0.16 m) of 3-hexyne-2,5-ditosylate were dissolved in a mixture of 1700 ml of ethanol and 750 ml of dioxan. To this solution, which was cooled in ice-water, a solution of 63 g potassium permanganate and 91 g of magnesium sulphate hepta hydrate in 1600 ml of water was added at 20°-22° C in the course of 45 min. Stirring was continued for 30 min. and 600 ml of water were added and the brown reaction mixture was extracted five times with 200 ml portions of cold chloroform. The combined extracts were washed with water dried over anhydrous sodium sulphate and evaporated. The solid residue was recrystallized from tetrachloromethane affording 46 g = 64% of yellow crystals with m.p. 128°-130° (dec.) 23 g of hexane-3,4-dione-2,5-ditosylate were dissolved in a mixture of 30 ml water and 50 ml ethanol at 90° C. To this solution was added 18 g of sodium sulphide nonahydrate. The mixture was stirred at 90° for 1.5 hours and then diluted with 300 ml water. After acidification with diluted hydrochloric acid, the mixture was extracted five times with dichloromethane. The combined extracts were washed with water, dried over sodium sulphate and evaporated. The crystalline residue was recrystallized from dichloromethane-light petroleum; yield = 4.32 g = 60%, m.p. = 77°-79° C.

Infra-red absorption characteristics; maxima at 3300, 2980, 2940, 1670, 1600, 1450, 1430, 1395, 1360, 1265, 1130, 1052, 955, 840, 760 cm⁻¹.

| NMR data: | δ | M | |
|---|---|---|---|
| | a : 1,55 | doublet | 3H |
| | b : 2,26 | multiplet | 3H |
| | c : 3,70 | " | 1H |
| | d : 5,6 | broad singulet | 1H |
| mass data: | m/e | i.% | m/e | i.% | m/e | i.% | m/e | i.% |
| i = intensity | 145 | 10 | 61 | 12 | 58 | 15 | 45 | 15 |
| | 144 | 60 | 60 | 25 | 57 | 19 | | |
| | 85 | 32 | 59 | 100 | 55 | 15 | | |

EXAMPLE A3

Preparation of a 4-hydroxy-2-ethyl-5-methyl-2,3-dihydrothiophene-3-one 0.5 mole of 1-butyn-3-ol was coupled with 0.5 mole of propionaldehyde under the influence of ethylmagnesium bromide according to Bull.Soc.Chim.(Fr.) 425 (1956) and 3-heptyne-2,5-diol (b.p. 109°–110° C at 2 mm Hg) was obtained in 64% yield. The alkyne diol was esterified with p-toluene sulfonylchloride as described in Example 1A and 3-heptyne-2,5-ditosylate (m.p. 69.5°–70.5° C) was obtained in 76% yield. The alkyne ditosylate was oxidised with aqueous potassium permanganate as described in Example 2A, at a temperature of 5° C and heptane-3,4-dione-2,5-ditosylate was obtained in 55% yield; m.p. 120°–121.5° C (from tetrachloromethane).

9.36 grams (0.02 m) of heptane-3,4-dione-2,5-ditosylate were dissolved in 200 ml of tetrahydrofuran at 40° C. In the course of 45 min. to this solution were added 4.5 grams (0.02 m) of sodium sulphide nonahydrate dissolved in 50 ml of water. The mixture was stirred for 15 minutes at 40° C and then acidified to pH 5.5 with aqueous hydrochloric acid. The mixture was extracted five times with dichloromethane and the combined extracts were washed with water, dried over sodium sulphate and evaporated. The residue was chromatographed over a polyamide columm (50 × 2 cm). Elution with dichloromethane afforded the product in 40% yield, which was pure according to gaschromatographic analysis.

Infra-red absorption characteristics: maxima at 3350, 2965, 2925, 2870, 1670, 1600, 1455, 1435, 1400, 1360, 1280, 1260, 1135, 1060, 1025, 970, 945, 885, 860, 775, 760, 750 cm$^{-1}$.

| mass data: | m/e | i.% | m/e | i.% |
|---|---|---|---|---|
| i = intensity | 158 | 100 | 57 | 65 |
| | 130 | 80 | 43 | 50 |
| | 99 | 63 | 41 | 48 |
| | 85 | 63 | 39 | 43 |
| | 73 | 100 | | |
| | 59 | 62 | | |

EXAMPLE A4

Preparation of 4-mercapto-5-methyl-2,3-dihydrothiophene-3-one and 4-mercapto-5-methyl-2,3-dihydrofuran-3-one A mixture of 2 g of 4-hydroxy-5-methyl-2,3-dihydrothiophene-3-one, 60 ml of liquid hydrogen sulphide and 200 ml of water was placed in an autoclave and the whole was heated at 100° C for 4 hours. After cooling, the flavouring mixture thus obtained was extracted five times with dichloromethane and the combined extracts were washed and dried over anhydrous sodium sulphate, concentrated to about 10 ml and allowed to stand overnight in the refrigerator. The precipitate formed was collected by filtration, washed and dried to give 0.8 g of starting material.

From the mother liquor 0.5 g of the title compounds were isolated by preparative gaschromatography, using a column of 600 × 0.4 cm, a support of Diatoport S (a silanated silicagel) ex Hewlett Packard loaded with 1% Carbowax 20 M (a polyethylene glycol ether with a molecular weight above 20,000) ex Hewlett Packard and 10% Apiezon (a mixture of stable alkanes) ex Shell Comp. Nitrogen was used as a carrier gas at a velocity of 40 ml per minute. The temperature was programmed; starting temperature 60° C; Increase in temperature 4° per minute. The retention time found for 4-mercapto-5-methyl-2,3-dihydrofuran-3-one was 34.0 minutes and for 4-mercapto-5-methyl-2,3-dihydrothiophene-3-one 53.4 minutes as compared with 27.2 and 32.5 minutes for decane and undecane respectively.

Infra-red absorption characteristics of 4 mercapto-5-methyl-2,3-dihydrofuran-3-one: maxima at 2920, 2850, 2530 (weak), 1510, 1435, 1375, 1175, 1090, 890, 855, 715 cm$^{-1}$.

| Mass data: | m/e | i.% | m/e | i.% |
|---|---|---|---|---|
| i = intensity | 132 | 10 | 96 | 10 |
| | 131 | 14 | 85 | 14 |
| | 130 | 100 | 59 | 12 |
| | 129 | 46 | 52 | 39 |
| | 98 | 10 | 51 | 36 |
| | 97 | 51 | 50 | 27 |
| | | | 45 | 28 |

Infra-red absorption characteristics of 4-mercapto-5-methyl-2,3-dihydrothiophene-3-one: maxima at 2920, 2860, 2530, 1665, 1565, 1450, 1395, 1375, 1265, 1200, 1150, 1085, 860, 800, 730 cm$^{-1}$.

| mass data: | m/e | i.% | m/e | i.% | m/e | i.% | m/e | i.% |
|---|---|---|---|---|---|---|---|---|
| i = intensity | 148 | 11 | 114 | 28 | 71 | 25 | 55 | 20 |
| | 147 | 10 | 113 | 35 | 69 | 10 | 53 | 15 |
| | 146 | 100 | 100 | 16 | 61 | 12 | 47 | 10 |
| | 145 | 20 | 99 | 18 | 60 | 25 | 46 | 12 |
| | 132 | 15 | 98 | 13 | 59 | 95 | 45 | 63 |
| | 130 | 40 | 97 | 43 | 58 | 30 | | |
| | 129 | 15 | 85 | 40 | 57 | 10 | | |

EXAMPLE A5

Preparation of 4-mercapto-2,5-dimethyl-2,3-dihydrothiophene-3-one 12.8 grams (0.1 m) of 4 hydroxy-2,5-dimethyl-2,3-dihydrofuran-3-one were dissolved in 70 ml of dry pyridine. The solution was stirred and cooled to −10° C in an ice-salt bath. With stirring a cold solution of 22.9 grams (0.12 m) of p-toluene sulfonylchloride in 50 ml of dry dichloromethane was added dropwise (temp. below −5° C). After completion of the addition (1 hour), stirring at 0° C was continued for 3 hours, and water (10 ml) was added in portions at intervals of 5 min., with stirring and cooling, so that the temperature did not rise above 5° C. The solution was then poured into 250 ml of ice-water. The mixture was extracted four times with dichloromethane, the combined extracts were successively washed with portions of ice-cold dilute sulphuric acid, water, sodium hydrogen carbonate solution and water. The dichloromethane solution is then dried with anhydrous sodium sulphate and evaporated to dryness. Crystallization from ethanol yielded 21.3 grams = 75.5% of the pure 4-p-toluene-sulfonyloxy-2,5-dimethyl-2,3-dihydrofuran-3-one with m.p. 70°–72° C. 3.5 grams (12.4 mmol) of the tosylate thus obtained were dissolved in a mixture of 15 ml of ethanol and 5 ml of water at 40° C. To this solution was added a solution of 1.68 grams (30 mmol) of sodium hydrogensulphide in 20 ml of ethanol, while a gentle stream of hydrogen sulphide was passed through the reaction mixture. After completion of the addition, which took one hour, stirring and passing of H$_2$S into the solution were continued for 6 hours at 40° C and the reaction mixture was diluted with 200 ml of water, acidified with aqueous dilute hydrochloric acid (pH 5.5) and continuously extracted with ether for 18 hours. The extract was dried over anhydrous sodium sulphate and evaporated to dryness. From the residue the title compound was isolated in a quantity of 3 grams by preparative gaschromatography, using a column of 600 × 0.4 cm, a support of Diatoport S (a silanated silicagel) ex Hewlett Packard, loaded with 1% Carbowax 20 M (a polyethylene glycol ether with a molecular weight above 20,000) ex Hewlett Packard and 10% Apiezon (a mixture of stable alkanes) ex Shell Comp. Nitrogen was used as a carrier gas at a velocity of 40 ml per minute.

The temperature was programmed; starting temperature 60° C; Increase in temperature 4° per minute. The retention time found for 4-mercapto-2,5-dimethyl-2,3-dihydrothiophene-3-one was 40.1 minutes.

Infra-red absorption characteristics of 4-mercapto-2,5-dimethyl-2,3-dihydrothiophene-3-one: maxima at 2980, 2920, 2860, 2530, 1670, 1565, 1460, 1390, 1375, 1275, 1255, 1130, 1000, 930, 875, 770, 740 and 540 cm$^{-1}$.

| mass data: | m/e | i.% | m/e | i.% | m/e | i.% |
|---|---|---|---|---|---|---|
| i = intensity | 162 | 12 | 111 | 25 | 67 | 26 |
|  | 160 | 100 | 99 | 26 | 61 | 31 |
|  | 159 | 10 | 85 | 18 | 60 | 34 |
|  | 127 | 26 | 72 | 30 | 59 | 95 |
|  | 117 | 17 | 71 | 30 | 58 | 25 |
|  |  |  |  |  | 57 | 28 |

EXAMPLE A6

Preparation of cis-3-mercapto-2-methyl-tetrahydrofuran 2.38 g (19.75 mmol) of trans 3-chloro-2-methyltetrahydrofuran, b.p. 130° C (atm.) $N_D^{20}$ 1.4908, prepared according to the method described by L. Crombie and S. H. Harper, J. Chem. Soc. 1714 (1950) were dissolved in 20 ml of dimethylformamide. 3.42 g (30 mmol) of potassium thiolacetate were added to the solution and the mixture was refluxed for one hour. After cooling, the solvent was distilled off in vacuum and the residue dissolved in 50 ml of water. The aqueous solution was extracted three times with chloroform and the combined extracts were washed with water, dried over anhydrous sodium sulphate and evaporated. The residue was distilled through a 10 cm Vigreux column, yielding 1.71 g of cis. 3-thioacetoxy-2-methyltetrahydrofuran (54%) b.p. = 52°-53° C/0.2 mmHg.

1.5 g (9.2 mmol) of cis-3-thioacetoxy-2-methyltetrahydrofuran was dissolved in 46 ml of a methanol solution of 0.4 M sodium methoxide and the mixture was allowed to stand overnight at room temperature.

Thereafter the reaction mixture was acidified with aqueous sulfuric acid and extracted several times with chloroform. The combined chloroform extracts were washed with water, dried over sodium sulphate and evaporated. The residue was fractionated, using a 10 cm Vigreux column, yielding 0.72 g (67%) of cis-3-mercapto-2-methyl tetrahydrofuran, b.p. 64°-65° C/13 mmHg, $n_D^{20}$ = 1.4904

Infra-red absorption characteristics of cis-3-mercapto-2-methyl-tetrahydrofuran: maxima at 2975, 2930, 2870, 2540, 1453, 1385, 1355, 1320, 1110, 1070, 1020, 990 and 850 cm$^{-1}$.

| mass data: | m/e | i.% | m/e | i.% |
|---|---|---|---|---|
| i = intensity | 84 | 30 | 55 | 40 |
|  | 74 | 100 | 46 | 30 |
|  | 73 | 20 | 45 | 80 |
|  | 59 | 20 | 43 | 90 |
|  | 56 | 25 | 41 | 100 |

Relative retention time as compared with 43.1 minutes found for dodecane was 29.2 minutes.

EXAMPLE A 7

Preparation of trans-3-mercapto-2-methyltetrahydrofuran

By the procedure used for the cis-isomer (cf. previous example) 3.92 g (32.5 mmol) of cis-3-chloro-2-methyl tetrahydrofuran b.p. 145° C (atm.) $n_D^{20}$ 1.4520, were treated with potassium thiolacetate affording 2.34 g (45%) of trans-3-thio-acetoxy-2-methyl-tetrahydrofuran b.p. 49°-50° C/3 mmHg. This product (1.8 g) was hydrolysed with sodium methoxide as described in the previous example, yielding 0.85 g of trans-3-mercapto-2-methyltetra hydrofuran b.p. 62° C/20 mmHg, $n_D^{20}$ = 1.4798.

Infra-red absorption characteristics: maxima at 2975, 2930, 2870, 2540, 1453, 1385, 1355, 1195, 1140, 1120, 1075, 1018 and 860 cm$^{-1}$.

| mass data: | m/e | intensity % | m/e | intensity % |
|---|---|---|---|---|
|  | 84 | 30 | 55 | 40 |
|  | 74 | 100 | 46 | 30 |
|  | 73 | 20 | 45 | 80 |
|  | 59 | 20 | 43 | 90 |
|  | 56 | 25 | 41 | 100 |

Relative retention time as compared with 43.1 minutes found for dodecane was 25.5 minutes.

EXAMPLE A 8

Preparation of cis and trans-3-mercapto-5-methyl-tetrahydrofuran.

5 g (50 mmol) of 3-hydroxy-5-methyltetrahydrofuran, b.p. 92° C/23mmHg, prepared according to the method of F. C. Hartman and R. Baker, J. Org. Chem. 29, 873 (1964), were dissolved in 30 ml of pyridine and 11.5 g(60 mmol) of p-toluene-sulfonylchloride were added at −10° C. The mixture was allowed to stand for 18 hours at roomtemperature, the reaction mixture was worked up in the usual way, yielding 11.6 g (90%) 3-p-tolyl sulfonyloxy-5-methyl-tetrahydrofuran-10 g of the p-toluenesulfonate were dissolved in 80 ml of acetone and treated with 5.7 g (50 mol) of potassium thiolacetate. After the reaction mixture had remained at reflux temperature for 24 hours, the acetone was removed by evaporation. The residue was dissolved in water and the aqueous solution extracted three times with dichloromethane; the combined extracts were washed, dried and evaporated to dryness. Distillation of the residue gave 5.55 g (89%) of the 3-thioacetoxy-5-methyltetrahydrofuran, b.p. 62°-63° C/1.3 mmHg.

4.0 g (25 mmol) of the thiolacetate was hydrolysed as described in Example A 6, yielding 2.38 g (80%) of the cis/trans 3-mercapto-5-methyl-tetrahydrofuran b.p. 57°-58° C/14 mmHg; $n_D^{20}$ = 1.4795. Infra-red absorption characteristics: maxima at 2970, 2925, 2860, 2540, 1440, 1380, 1350, 1080, 1050, 1015, 890 and 810 cm$^{-1}$.

| mass data: | m/e | Intensity (%) | m/e | Intensity (%) |
|---|---|---|---|---|
|  | 85 | 46 | 54 | 21 |
|  | 73 | 33 | 47 | 20 |
|  | 60 | 20 | 45 | 48 |
|  | 59 | 17 | 43 | 72 |
|  | 55 | 100 | 41 | 100 |

Relative retention times as compared with 43.1 minutes found for dodecane were 27.3 minutes for the trans compound and 27.7 minutes for the cis compound.

EXAMPLE A 9

Preparation of 3-mercapto-2-methyl-4,5-dihydrofuran 13.65 g (0.1 m) of 3-chloro-3-acetylpropanol (b.p. 90°-110° C/2mmHg; $n_D^{20}$ 1.4740) prepared according to the method described by J. R. Stevens and G. A. Stein, J.Am.Chem.Soc. 62, 1045 (1940), were refluxed with 18.6 g (0.15 m) potassium thiolacetate in 100 ml of acetone for about 2 hours. After cooling the reaction mixture was filtered and the filtrate evaporated to dryness and the residue dissolved in water. The aqueous solution was extracted five times with chloroform and the combined extracts washed, dried and evaporated. Distillation of the residue yielded 3-thioacetoxy-2-methyl-4,5-dihydrofuran, b.p. 57°-59° C/0.6 mmHg.

5 g (31.6 mol) of 3-thioacetoxy-2-methyl-4,5-dihydrofuran were dissolved in 156 ml of a 0.4 N sodium methoxide in methanol and left at room temperature for 24 hours. The reaction product was purified in the usual way affording the title compound which could be isolated by preparative gas chromatography. Infra-red absorption characteristics: maxima at 2960, 2920, 2890, 2860, 1740, 1663, 1635, 1480, 1435, 1400, 1380, 1365, 1220, 1060, 1030, 980, 960, 905, 680 cm$^{-1}$.

| mass data: | m/e | Intensity (%) | m/e | Intensity (%) |
|---|---|---|---|---|
| | 116 | 70 | 60 | 24 |
| | 84 | 22 | 45 | 55 |
| | 83 | 20 | 43 | 100 |
| | 73 | 36 | 42 | 20 |
| | 71 | 19 | 41 | 20 |

Relative retention time as compared with 43.1 minutes found for dodecane was 30.6 minutes.

EXAMPLE A 10

Preparation of 3-mercapto-5-methyl-4,5-dihydrothiophene.

2 g of 5-methyl-tetrahydrothiophene-3-one (b.p. 68°-69.5° C/11 mmHg; $n_D^{20}$ 1.5062) prepared according to the method described by M. A. Gianturco, c.s., Tetrahedron, 20 1763 (1964) were dissolved in 25 ml of ethanol (saturated with hydrogen chloride) and treated with hydrogensulphide at −80° C according to the method given by S. Bleisch and Mayer, Chem.Ber. 100, 100 (1967). After purification of the reaction mixture the title compound could be isolated by preparative gas chromatography.

Infra-red absorption characteristics: maxima at 2960, 2920, 2860, 2510, 1540, 1445, 1425, 1400, 1375, 1260, 1205, 1080, 930, 825, 790, 720, 680 cm$^{-1}$.

| mass data: | m/e | Intensity (%) | m/e | Intensity (%) |
|---|---|---|---|---|
| | 132 | 100 | 84 | 36 |
| | 117 | 95 | 59 | 38 |
| | 99 | 58 | 58 | 28 |
| | 97 | 38 | 45 | 100 |
| | 85 | 37 | 41 | 42 |

Relative retention time as compared with 43.1 minutes found for dodecane was 43.1 minutes.

EXAMPLE A 11

Preparation of 3-mercapto-5-methyl-4,5-dihydrofuran 2.75 g 5-methyl-tetrahydrofuran-3-one, b.p. 88°-89° C/112 mmHg, prepared according to the method described by H. Wijnberg, J. Amer. Chem.Soc. 80, 364 (1958), were dissolved in 3.5 ml of ethanol (saturated with HCl gas). The solution was cooled to −80° C and treated with hydrogen sulphide as described by R. Mayer, Angew. Chem., Intern. Edition 3, 277 (1964).

After purification of the reaction product, the title compound was isolated by distilltion at reduced pressure under nitrogen and by preparative gas chromatography.

Infra-red absorption characteristics: maxima at 2980, 2930, 2862, 2540, 1620, 1455, 1385, 1270, 1235, 1110, 1080, 1050, 1035, 945, 899, 825, 650 cm$^{-1}$.

| mass data: | m/e | i.% | m/e | i.% | m/e | i.% |
|---|---|---|---|---|---|---|
| | 116 | 17 | 55 | 11 | 42 | 50 |
| | 73 | 13 | 45 | 32 | 41 | 26 |
| | 72 | 22 | 43 | 100 | 39 | 25 |
| | 71 | 34 | | | | |

Relative retention time as compared with 43.1 minutes found for dodecane was 29.0 minutes.

EXAMPLE A 12

Preparation of 3-mercapto-2,5-dimethyl-4,5-dihydrofuran.

2.0 g 2.5-dimethyl-tetrahydrofuran-3-one (b.p. 143° C/atm.; $n_D^{20}$ 1.4240) prepared according to the method described by G. Dupont, Ann. de Chimie et de Physique, 8$^e$ serie, Tome 30, 535 (1913) were converted into the title compound with hydrogen sulphide as described in Example A 11. From the reaction product the title compound was isolated by preparative gas chromatography.

Infra-red absorption characteristics: maxima at 2975, 2925, 2862, 2540, 1610, 1460, 1450, 1378, 1330, 1262, 1218, 938, 875, 830 cm$^{-1}$.

| mass data: | m/e | i.% | m/e | i.% | m/e | i.% |
|---|---|---|---|---|---|---|
| | 130 | 14 | 55 | 10 | 43 | 100 |
| | 88 | 10 | 53 | 14 | 41 | 13 |
| | 87 | 12 | 45 | 20 | 39 | 14 |
| | 71 | 24 | | | | |

Relative retention time as compared with 43.1 minutes found for dodecane was 28.5 minutes.

EXAMPLES A 13

Preparation of 3-mercapto-2,5-dimethyl-4,5-dihydrothiophene 2.5-dimethyl tetrahydrothiophene-3-one (b.p. 72°-82° C/12 mmHg; $n_D^{20}$ 1.4908) were prepared according to the method described by H. A. Gianturco, Tetrahedron 64, 1763 (1964) from 4.6 (0.2 mol) sodium, 26 g (0.2 m)methyl-α-mercaptopropionate and 22 g (0.22 mol) methylcrotonate. After purification the reaction product yielded 39 of an oily residue which, upon distillation, gave 21.7 g (58%) 2.5-dimethyl-3-carbomethoxy tetrahydrothiophene-4-one, b.p. 80–84%/0.2mmHg. The decarboxylative hydrolysis of the b-ketoester was effected by refluxing for 1 hour in 10% aqueous H2SO4. After purification the reaction product yielded 2.5-dimethyl-tetrahydrothiophene-3-one in nearly quantitative yield; b.p. 80° C/12 mmHg.

The ketone prepared as mentioned above was converted into the title compound and could be isolated by preparative gas chromatography. Infra-red absorption characteristics: maxima at 2960, 2920, 2882, 2837, 1450, 1440, 1290, 1250, 1210, 1152, 1015, 1000, 688 cm$^{-1}$.

| mass data: | m/e | i.% | m/e | i.% |
|---|---|---|---|---|
| i = intensity | 146 | 90 | 61 | 25 |
| | 131 | 44 | 59 | 100 |
| | 113 | 60 | 45 | 55 |
| | 98 | 38 | 41 | 28 |
| | 85 | 24 | 39 | 36 |

Relative retention time as compared with 43.1 minutes found for dodecane was 43.1 minutes.

EXAMPLE A 14

Preparation of cis/trans 3-mercapto-2-methyl tetrahydrothiophene.

23.2 g (0.2 m) of 2-methyl-tetrahydrothiophene-3-one (b.p. 68°-70° C/11 mmHg; $n_D^{20}$ 1.5079) prepared according to the method described by P. Karrer and H. Schmid, Helv. Chim. Acta 27, 124 (1944), dissolved in 150 ml of dry ether were added dropwise in the course of 45 min. to a suspension of 7.8 g (0.2 m) of LiAlH4 in 300 ml of dry ether.

After the addition was completed the reaction mixture was refluxed for 2 hours under nitrogen cooled in an ice-bath and a mixture of 30 ml of ethylacetate and 100 ml of ether were added. After filtration, the organic layer was washed with water, dried and evaporated. From the residue the cis/trans mixture of 3-hydroxy-2-methyl-tetrahydrothiophene could be isolated.

The cis/trans mixture of the alcohols prepared as mentioned above was converted into their p-toluene sulphonates by the method described earlier.

The p-toluene sulfonic esters were treated with potassium thioacetate in acetone as described for the preparation of Example A 8 and purified in the usual way. After hydrolysation of the thioacetate with sodium methoxide in methanol for 18 hours at room temperature, water was added and the liquid was extracted with CH$_2$Cl$_2$. After acidification the aqueous phase was again extracted with CH$_2$Cl$_2$. The organic layer was dried with Na$_2$SO$_4$ and evaporated, yielding cis/trans 3-mercapto-2-methyl-tetrahydrothiophene. The isomers were isolated by gas chromatography as described above.

Infra-red absorption characteristics: cis:maxima at 2962, 2920, 2895, 2865, 1456, 1442, 1376, 1315, 1260, 1200, 1170, 1020, 960, 680. trans:2962, 2925, 2880, 2850, 1450, 1440, 1379, 1330, 1270, 1200, 670 cm$^{-1}$.

| mass data: | cis-compound | | trans-compound | |
|---|---|---|---|---|
| i = intensity | m/e | i.% | m/e | i.% |
| | 134 | 32 | 134 | 82 |
| | 85 | 19 | 74 | 70 |
| | 74 | 38 | 69 | 54 |
| | 69 | 20 | 67 | 35 |
| | 59 | 27 | 59 | 26 |
| | 55 | 28 | 55 | 48 |
| | 47 | 28 | 47 | 26 |
| | 45 | 52 | 45 | 36 |
| | 41 | 100 | 41 | 100 |
| | 39 | 47 | 39 | 45 |

Relative retention time as compared with 43.1 minutes found for dodecane was for cis 41.6 and for trans 43.8.

EXAMPLE A 15

Synthesis of cis/trans 3-mercapto-5-methyl-tetra hydrothiophene.

23.3 g (0.2 m) of 5-methyl-tetrahydrothiophene-3-one b.p. 88°-89° C/112 mmHg were converted with LiAlH4 into the cis/trans mixture of 3-hydroxy-5-methyltetrahydrothiophene by the method described above.

From this alcohol/mixture the p-toluene sulfonic esters were made in the usual way and the latter were converted into the thioacetates and subsequently into the title compound by hydrolysation with sodium methoxide in methanol. The isolation of 3-mercapto-5-methyl tetrahydrothiophene was achieved by distillation and preparative gas chromatography; $n_D^{20}$ 1.5568.

Infra-red absorption characteristics:maxima at 2958, 2920, 2860, 2540, 1450, 1435, 1375, 1268, 1205, 1182, 1030, 1000, 940, 735, 715, 700 cm$^{-1}$.

| mass data: | m/e | i.% | m/e | i.% |
|---|---|---|---|---|
| i = intensity | 134 | 100 | 49 | 88 |
| | 86 | 42 | 45 | 45 |
| | 85 | 46 | 43 | 46 |
| | 84 | 62 | 41 | 52 |
| | 61 | 36 | | |
| | 59 | 38 | | |

Relative retention time as compared with 43.1 minutes found for dodecane was 40.5 minutes.

EXAMPLE A 16

Synthesis of 3-mercapto-2,5-dimethyltetrahydrofuran.

2.5-dimethyltetrahydrofuran-3-one, b.p. 143° C/atm., $n_D^{20}$ 1.4240, were reduced with LiAlH4 as described above, yielding a mixture of stereoisomers of 3-hydroxy-2.5-dimethyltetrahydrofuran. The latter were converted into the p-toluene sulfonic esters and then subsequently treated with potassium thioacetate. After hydrolysis of the thioactic ester with sodium methanolate the title compound was isolated by preparative gas chromatography.

Infra-red absorption characteristics: maxima at 2975, 2930, 2870, 2540, 1458, 1448, 1380, 1165, 1125, 1100, 1083, 951, 916, 880 cm$^-$.

| mass data: | m/e | i.% | m/e | i.% | m/e | i.% |
|---|---|---|---|---|---|---|
| i = intensity | 99 | 26 | 73 | 26 | 43 | 53 |
| | 98 | 19 | 60 | 24 | 39 | 14 |
| | 88 | 50 | 55 | 100 | | |
| | 83 | 8 | 45 | 18 | | |

Relative retention time as compared with 43.1 minutes found for dodecane was 20.0 minutes.

EXAMPLE A 17

Synthesis of 3-mercapto-2,5-dimethyltetrahydrothiophene.

2.5-dimethyltetrahydrothiophene-3-one, b.p. 143° C/atm., $n_D^{20}$ 1.4240, was reduced with LiAlH4, converted into the p-toluene sulfonic esters and the thioacetates, and finally into the title compound by the procedure as described above for the corresponding oxygen compound. The title compound was isolated by preparative gas chromatography.

Infra-red absorption characteristics: maxima at cis:2965, 2925, 2865, 1458, 1450, 1380, 1310, 1250, 1168, 1025, 1000, 992, 938, 680 trans:2965, 2920, 2860, 1455, 1448, 1378, 1270, 1190, 1168, 1020, 997, 985 cm$^{-1}$.

|  | cis compound | | trans compound | |
|---|---|---|---|---|
| mass data: | m/e | intensity (%) | m/e | intensity (%) |
|  | 148 | 36 | 148 | 48 |
|  | 99 | 33 | 99 | 29 |
|  | 67 | 40 | 67 | 46 |
|  | 61 | 90 | 61 | 88 |
|  | 60 | 39 | 60 | 39 |
|  | 59 | 70 | 59 | 67 |
|  | 55 | 100 | 55 | 100 |
|  | 45 | 68 | 45 | 53 |
|  | 41 | 80 | 41 | 70 |
|  | 39 | 72 | 39 | 58 |

Relative retention time as compared with 43.1 minutes found for dodecane was for cis 42.4 and for trans 44.7 minutes.

EXAMPLE A 18

Synthesis of 3-mercapto-2-methyl-4.5-dihydrothiophene.

2 g of 2-methyltetrahydrothiophene-3-one b.p. 68°–70° C/11 mmHg; $n_D^{20}$ 1.5079, prepared according to the method described by P. Karrer and H. Schmid, Helv. Chim. Acta, 27, 124 (1944), was dissolved in 25 ml of ethanol (saturated with hydrogen chloride) and treated with hydrogen sulphide at −80° C as described by R. Mayer, Angew. Chem., Intern. Edition, 3, 277 (1964). From the reaction product 3-mercapto-2-methyl-4,5-dihydrothiophene could be isolated by preparative gas chromatography.

Infra-red absorption characteristics: maxima at 2960, 2930, 2910, 2840, 1585, 1435, 1400, 1375, 1300, 1265, 1149, 1020, 850, 750, 685, 675 cm$^{-1}$.

| mass data: | m/e | i.% | m/e | i.% | m/e | i.% |
|---|---|---|---|---|---|---|
| i = intensity | 132 | 100 | 98 | 28 | 65 | 19 |
|  | 131 | 29 | 97 | 34 | 59 | 70 |
|  | 99 | 90 | 71 | 23 | 58 | 18 |
|  |  |  |  |  | 45 | 41 |

Relative retention time as compared with 43.1 minutes found for dodecane was 48.0 minutes.

EXAMPLE A 19

Synthesis of 2.5 - dimethyl-2.3 dihydrofuran-3-thione (3-mercapto 2.5-dimethylfuran).

56 mg of 2,5 -dimethyl-2,3-dihydrofuran-3-one b.p. 66° – 68° C at 10 mm mercury, $n_D^{22}$ = 1.4785 prepared according to the method described by I. I. Nazarova, B. P. Gusev and V. F. Kucherov, Izv. Akad. Nauk. SSSR, Ser Khim 1967 (7) 1580; Chem. Abstr. 68 2549 P, was refluxed with 111 mg of phosphor pentasulphide in 10 ml of toluene for 2 hours. The title compound was isolated by preparative gas chromatography.

Infra-red absorption characteristics: maxima at 3115, 2950, 2920, 2880, 2850, 1567, 1430, 1380, 1365, 1330, 1225, 1115, 1065, 1000, 980, 920, 795, 646 and 615 cm$^{-1}$.

| Mass data: | m/e | Intensity (%) | m/e | Intensity (%) |
|---|---|---|---|---|
|  | 129 | 4.5 | 95 | 10 |
|  | 128 | 65 | 85 | 25 |
|  | 127 | 22 | 45 | 10 |
|  | 113 | 8 | 43 | 100 |
|  | 96 | 4.5 | 39 | 9 |

Relative retention time as compared with 43.1 minutes found for dodecane was 42 minutes.

EXAMPLE B 1

4-hydroxy-5-methyl-2,3-dihydrofuran-3-one (0.5 g) was dissolved in water (30 ml) and reacted with hydrogen sulphide (15 g) for 4 hours at 95°–100° C in a glass-lined autoclave. At the end of the reaction period the mixture was cooled and poured into ice-water (100 ml) and extracted five times with dichloromethane. The combined extracts (125 ml) were concentrated at atmospheric pressure to 10ml and the concentrated dichloromethane extract was anlysed by gas-liquid chromatography on a 600 - 0,4 cm glass column with Diatoport S as support. The stationary phase was Apiezon L 10% and Carbowax 20 M 1%, the temperature was programmed from 60°–220° C at 4° C/min, the carrier gas was nitrogen with a velocity of 40 ml/min and the recorder speed was 48 cm/h. From the exhaust of the gas chromatograph the various microgram samples could be trapped and their infra-red spectra could be obtained from these samples according to the method described by H. Copier and J.H.v.d.Maas, Spectro Chemica Acta, 23A 2699 (1967).

The infra-red spectra were determined using a Perkin-Elmer 225 and 257 spectrometer. The mass data were determined using an A.E.I. MS-9 instrument at a source temperature of 200° C. with the following procedure: On one of the inlets of the mass spectrometer a capillary with 0.1 ml/minute conductance was mounted. The glass tubes with the absorbed eluent were connected to this capillary by a ground glass joint, a heater was placed around the sample tube and with a stream of helium the compound was flushed into the ion source of the mass spectrometer.

From the reaction mixture the following products could be isolated and identified:

| Mass data m/e and intensity % | Infra-red data (cm$^{-1}$) | Ret. time min.$^+$) | Assumed Structure |
|---|---|---|---|
| 114 (100), 113 (50) 85 (60), 71 (45), 69 (36), 59 (35), 53 (44), 51 (41), 45 (56), 43 (85) | 2950, 2920 2850,1585, 1560, 1518, 1510, 1440, 1387, 1225, 1195,1123, 1088, 1018, 940, 888, 730 | 26.6 | 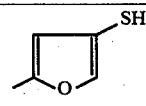 |
| 116 (70), 84 (22), 83 (20), 73 (36), 71 (19), 60 24., 45 (55), 43 (100), 42 (20), 41 (20). | 2960, 2920, 2890, 2860 1740, 1663, 1635, 1480, 1435, 1400, 1380, 1365, 1220, 1060, 1030, 980, 960, 905, 680. | 30,6 | 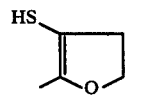 |
| Corresponding to data of Example A 11 |  |  | 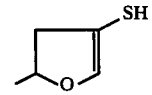 |

| Mass data m/e and intensity % | Infra-red data (cm⁻¹) | Ret. time min.+) | Assumed Structure |
|---|---|---|---|
| Corresponding to data of Example A 7 | | 25,5 | 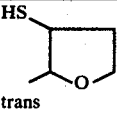 trans |
| Corresponding to data of Example A 6 | | 29,2 | 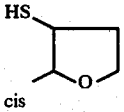 cis |
| Corresponding to data of Example A 8 | | 27,3 | 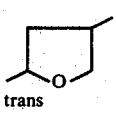 trans |
| Corresponding to data of Example A 8 | | 27,7 | 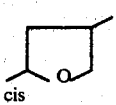 cis |
| 132 (20), 117 (100), 100 (12), 99 (12), 85 (25), 59 (40), 58 (14), 45 (30), 43 (12), 41 (27) | | 37,5 | 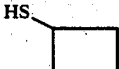 |
| 133 (62), 130 (60), 129 (55), 117 (47), 97 (65), 85 (55), 60 (67), 59 (94), 43 (35), 41 (52). | | 40,7 | 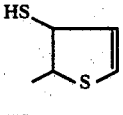 |
| 132 (48), 131 (41), 103 (31), 97 (58), 71 (45), 67 (35), 59 (35), 45 (85), 43 (100), 41 (53). | | 42,5 | 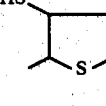 |
| 132 (48), 131 (41), 103 (31), 97 (58), 71 (45),67 (35), 59 (35), 45 (85), 43 (100), 41 (53), | 2960, 2910, 2850, 1725, 1645, 1420, 1378, 1255, 1115, 940, 780. | 48,1 | 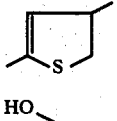 |
| Corresponding to data of Example A 1 | | 47.0 | 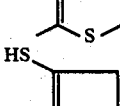 |
| Corresponding to data of Example A 18 | | 48 | 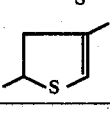 |
| Corresponding to data of Example A 10 | | 43,1 | 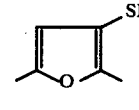 |

+)As compared with 43.1 min for dodecane.

EXAMPLE B2

4-hydroxy-2,5-dimethyl-2,3-dihydrofuran-3-one (0.5 g) was treated with hydrogensulphide (15g) and analysed as described in example B1. From the reaction product the following components were isolated and identified:

| Mass data | Infra-red data | Ret. time min+) | Structure |
|---|---|---|---|
| Corresponding to data of Example A 19 | | 42 | 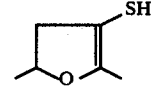 |
| Corresponding to data of Example A 12 | | 28.5 | 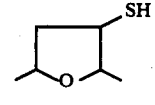 |
| Corresponding to data of Example A 16 | | 29.0 | 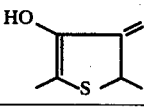 |
| Identical with data of Example A 2 | | 45.4 | 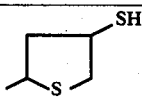 |

+) As compared with 43.1 min. for dodecane.

EXAMPLE B3

4-hydroxy-5-methyl-2,3-dihydrothiophene-3-one (0.5 g) was treated with hydrogen sulphide (15 g) as described in example B1. From the reaction product the following reaction components were isolated.

| Mass data | Infra-red data | Ret. time min.+) | Structure |
|---|---|---|---|
| Corresponding to data of Example A 15 | | 40.5 | 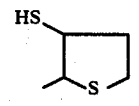 |
| Corresponding to data of Example A 14 | | cis 41.6 trans 43.8 | 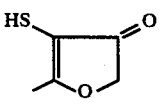 |
| Corresponding to data of Example A 4 | | 34++ | 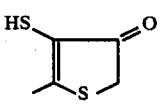 |
| Corresponding to data of Example A 4 | | 53.4++ | 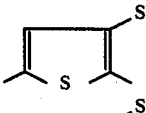 |

+)As compared with 43.1. minutes for decane.
+)As compared with 27.2 minutes for decane.

EXAMPLE B4

4-hydroxy-2,5-dimethyl-2,3-dihydrothiophene-3-one (0.5 g) was treated with hydrogen sulphide (15 g) as described in example B 1. From the reaction product the following components were isolated.

| Mass data | Infra-red data | Ret. time min. +) | Structure |
|---|---|---|---|
| 144 (60), 143 (36), 114 (27), 113 (21), 111 (52), 99 (59), 59 (100), 55 (29) (55), 41 (23). | 2958, 2920, 2860, 1445, 1378, 1315, 1190, 1153, 1132, 822, 680, 625, | 44.5 | 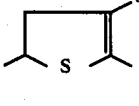 |
| Corresponding to data of Example A 13 | | 43.1 | 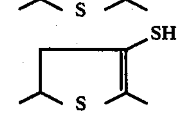 |

-continued

| Mass data | Infra-red data | Ret. time min. +) | Structure |
|---|---|---|---|
| | Corresponding to data of Example A 17 | cis 42.4 trans 44.7 | 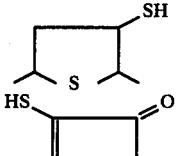 |
| | Corresponding to data of Example A 5 | | 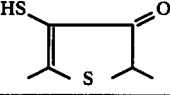 |

+) As compared with 43.1 min. for dodecane.

EXAMPLE C1

A beef-flavoured composition was prepared by adding 250 ml of water to a mixture of 5.7 g of 4-hydroxy-5-methyl-2,3-dihydrofuran-3-one and 25.0 g of cysteine and heating the mixture at about 100° C for 2½ hours. The resulting mixture was cooled and quantities of between 0.2 and 2.0 ml of the reaction mixture were sprayed over 100 g portions of dehydrated textured vegetable protein containing no meat. An excellent roast meat flavour was thereby imparted to this material as assessed by eleven out of a total panel of twelve expert tasters.

Dextrin-maltose was added to a portion of the flavoured mixture which resulted from the reaction described above in an amount which provided a composition containing about 70 parts by weight of dextrinmaltose to each part of the substance calculated on a solid basis. The composition was freeze-dried and a beef-flavoured product was obtained.

EXAMPLE C2

To 6.4 g of 4-hydroxy-2,5-dimethyl-2,3-dihydrofuran-3-one in a buffer solution containing about 35 g sodium acetate, about 14 g of acetic acid and 400 ml of water (pH 5.0), a solution of 12 g of sodium sulphide ($Na_2S.9H_2O$) in 200 ml of water was added over a period of 30 minutes. The mixture was then boiled under reflux conditions at atmospheric pressure for 2 hours and allowed to cool. The pH was then 6.6. The reaction mixture so obtained had a good roasted meat flavour.

EXAMPLE C3

A mixture of 7.2 g of 4-hydroxy-2-hydroxymethyl-5-methyl-2,3-dihydrofuran-3-one, 12 g of sodium sulphide ($Na_2S.9H_2O$) and 300 ml of water was heated in a round-bottomed flask fitted with reflux condenser for 2 hours at a temperature of 110° C. The reflux condenser was then removed and the contents cooled to room temperature. The resulting solution had a taste resembling that of roasted meat.

EXAMPLE C4

6.3 g of 3-hydroxy-2-methyl-1,4pyrone, 3.8 g of thioacetamide and 100 ml of water were heated together in a round-bottomed flask at 100° C for 2½ hours. The reaction mixture was then allowed to cool (pH 4.3) and it was shown to have an excellent roast beef flavour.

EXAMPLE C5

A roast beef-flavoured composition was prepared by adding 200 ml of water to a mixture of 7.0 g of 3-hydroxy-2-ethyl-1,4-pyrone and 4.6 g of mercaptoacetamide and heating the mixture to 100° C for 5 hours. A product having a good roasted meat flavour was obtained. Before use in conjunction with the foodstuff, the pH was adjusted to 5.5 by the addition of sodium hydroxide solution.

EXAMPLE C6

3.0 of a 70/30 mixture of 4-hydroxy-2-methyl-5-ethyl-2,3-dihydrofuran-3-one and 4-hydroxy-5-methyl-2-ethyl-2,3-dihydrofuran-3-one, 9.0 g of crysteine and 60 ml of water were heated in a round bottomed flask fitted with reflux condenser for 2 hours at 100° C. The reflux condenser was then removed and the contents cooled to room temperature. The resulting solution had a good roasted meat flavour.

EXAMPLE C7

A composition with a meat-like flavour was prepared by adding 100 ml of water to a mixture of 4.0 g of 4-hydroxy-2,5-diethyl-2,3-dihydrofuran-3-one and 20.0 g of cysteine and heating the mixture at 95°–100° C for 4 hours.

EXAMPLE C8

A mixture of 1.5 g of 4-hydroxy-5-methyl-2,3-dihydrofuran-3-one and 1.5 g of cysteine in 30 ml of water was heated at about 100° C for 2½ hours. To the resulting solution was added 33 g of maltodextrin. The solution thus obtained was carefully freeze-dried. The powder obtained was used as a good beef flavour in soup or gravy.

EXAMPLE C9

6.3 g of 3-hydroxy-2-methyl-1,4-pyrone, 10.5 g of sodium sulphide ($Na_2S9H_2O$) and 100 ml of water were heated together in a roundbottomed flask at 100° C for 2½ hours.

To the reaction mixture was added 117 g of maltodextrin. The resulting solution was spray-dried immediately. The powder thus obtained proved to have a good beef flavour.

EXAMPLE C10

5.0 of 4 hydroxy-2,5-dimethyl-2,3-dihydrofuran-3-one, 0.5 g of hydrogen sulphide and 100 ml of water were placed in an autoclave and heated for 2 hours at 100° C. To the resulting solution was added 100 g of malto-dextrin. The solution thus obtained was carefully freeze-dried. The powder obtained was used as a beef flavour in soup.

EXAMPLE C11

1.6 g of 4-hydroxy-2,5-dimethyl-2,3-dihydrofuran-3-one, 8.0 g of glutathione and 50 ml of water were heated for 1½ hours at 100° C in a round-bottomed flask fitted with a reflux condenser. To the resulting solution was added 5.0 g cysteine, and the mixture was again heated for 2 hours at 100° C. The resulting solution had a good roasted meat flavour.

EXAMPLE C12

A mixture of 4 g of powdered casein hydrolysate, 2 g of cysteine, 1 g of xylose, 1 g of 4-hydroxy-5-methyl-2,3-dihydrofuran-3-one and 50 ml of water was heated in a flask with stirring for 2½ hours at 95° C. The solution thus obtained proved to have a good beef flavour.

EXAMPLE C13

A mixture of 5 g 4-hydroxy-5-methyl-2,3-dihydrothiophene-3-one/Cf. Example A1), 0,5 g of hydrogen sulphide and 50 ml of water was heated in an autoclave for 4 hours at 100° C and was subsequently allowed to cool. A product with a roasted meat flavour was obtained which was diluted to a volume of 1 liter, forming a liquid meat flavour.

EXAMPLE D1

A dry goulash soup was prepared by mixing the following ingredients:

|  | grams |
|---|---|
| Dried meat | 5 |
| Salt | 8 |
| Monosodium glutamate | 2 |
| Protein hydrolysate | 1 |
| Dried onion | 5 |
| Toasted onion | 5 |
| Tomato powder | 4 |
| Paprika powder | 3 |
| Beef tallow | 10 |
| Corn starch | 25 |
| Herbs and spices | 4 |

According to this recipe two portions were prepared, each portion was used to make one liter of goulash soup by boiling it with 1 l of water for 20 minutes. To the first portion 0.5 ml of ethanol was added, whereas to the second portion 0.5 ml of ethanol containing 5 mg 3-mercapto-2-methyl-tetrahydrofuran (Cf. Example A7) were added. Both soups were compared by a panel consisting of 12 persons. The majority of the panel preferred the soup in which the 3-mercapto-2-methyltetrahydrofuran had been incorporated. The panel indicated as the reason for this preference the more pronounced meat-like flavour of the relevant product.

EXAMPLE D2

A chicken soup was prepared with the following ingredients:

|  | grams |
|---|---|
| Salt | 7 |
| Monosodium glutamate | 1 |
| Meat extract | 2 |
| Protein hydrolysate | 1 |
| Chicken bits | 4 |
| Noodles | 25 |
| Chicken fat | 7 |
| Herbs and spices | 4 |

These ingredients were boiled with 1 l of water for 10 minutes, after which a solution of 0.1 mg of 3-mercapto-5-methyltetrahdrofuran (Cf. Example A8) in 0.5 ml of ethanol was added. This resulted in a soup with a fuller, more pronounced chicken flavour, compared with the soup without added flavour.

EXAMPLE D3

A gravy was prepared from the following ingredients:

|  | grams |
|---|---|
| Potato starch | 15 |
| Onion powder | 2.5 |
| Monosodium glutamate | 3 |
| Beef tallow | 20 |
| Flour | 15 |
| Caramel | 1.6 |
| Pepper | 0.02 |
| Bay-leaves | 0.02 |
| Clove | 0.02 |
| Sodiumchloride | 8 |
| Protein hydrolysate | 4 |
| Beef extract powder | 2 |
| Tomato powder | 1 |

The potato starch and flour were added to the molten beef tallow under continuous stirring. The other ingredients were well blended and likewise added to the beef tallow. The whole mixture was boiled in 1 l of water. The gravy so obtained was devided in two portions of 500 ml. To the first portion 0.5 ml of ethanol was added and to the second portion 2.5 mg of 3-mercapto-2-methyl-4,5-dihydrofuran (Cf. Example A9) dissolved in 0.5 ml of ethanol.

Both gravies were compared by a panel consisting of 14 persons. The gravy containing 3-mercapto-2-methyl-4,5-dihydrofuran was preferred by 12 persons because of its more pronounced meaty flavour.

EXAMPLE D4

A seasoning powder was prepared with the following ingredients:

|  | grams |
|---|---|
| Meat extract powder | 4 |
| Salt | 5 |
| Monosodium glutamate | 3 |
| 5 Ribo-nucleotides | 0.1 |
| Protein hydrolysate | 2 |
| Onion powder | 0.2 |
| Celery salt | 0.2 |
| Pepper | 0.02 |
| Malto-dextrin | 0.3 |

A second seasoning powder was prepared according to this recipe. The only difference was that in this case the malto-dextrin contained 10 mg of 3-thioacetoxy-2-methyl-4,5-dihydrofuran per gram (Cf. Example A9). 12 g of both seasoning powders were dissolved in 1 l of hot water and assessed by a panel consisting of 12 persons. The seasoning powder containing the 3-thioacetoxy-2-methyl-4,5-dihydrofuran was unanimously preferred because of its more pronounced meaty flavor.

EXAMPLE D5

A gravy was prepared from the following ingredients:

|  | grams |
|---|---|
| Potato starch | 30 |
| Onion powder | 5 |
| Monosodium glutamate | 6 |
| Tallow | 40 |
| Wheat flour | 30 |
| Caramel dye | 3.2 |
| Pepper | 0.04 |
| Bay leaf | 0.04 |
| Clove | 0.04 |
| Salt | 16 |

| | grams |
|---|---|
| Protein hydrolysate | 8 |
| Commercial meat extract powder | 4 |
| Tomato powder | 2 |

The tallow was molten and potato starch and wheat flour were added under continuous stirring. Subsequently the remaining ingredients were well mixed and also added and the mixture was made up with water to a volume of 2 liters and boiled for 10 minutes.

The gravy thus obtained was divided into two equal parts and to the first part a solution of 10 ml of water containing 10 mg of 4-hydroxy-2,5-dimethyl-2,3-dihydrothiophene-3-one (Cf. Example A2) were added, whereas to the other part 10 ml of water were added.

After mixing, both samples were tested by a panel consisting of 9 persons of which 8 preferred the sample containing the thiophene derivative.

EXAMPLE D6

A paprica meat sauce was prepared from the following ingredients:

| | grams |
|---|---|
| Fresh red paprica, chopped | 80 |
| Paprica powder | 12 |
| Onion, comminuted | 100 |
| Tomato puree | 30 |
| Salt | 15 |
| Pepper | 1 |
| Garlic powder | 0.1 |
| Hydrogenated animal fat | 30 |
| Wheat flour | 60 |
| Meat | 250 |
| Water up to | 1000 |

The meat was fried in the fat and the onion and paprica were added and stewed in the mixture. Subsequently 200 g of water and the remaining ingredients, with the exception of the wheat flour, were added and heated up to the boil. The wheat flour was mixed with another 200 g of water and this was added to thicken the sauce. The remainder of the water was then added.

The meat sauce thus obtained was divided into two equal parts, and to one of the samples 10 ml of water, in which 10 mg of 4-hydroxy-2,5-dimethyl-2,3-dihydrothiophene-3-one (Cf. Example A2) were dissolved, were added, whereas to the other sample 10 ml of pure water were added. Both sauces were tested by a panel consisting of 9 persons of which the majority preferred the sample containing the thiophene derivative.

EXAMPLE D7

A chicken soup mix was prepared with the following ingredients:

| | grams |
|---|---|
| Salt | 3 |
| Monosodium glutamate | 2 |
| Sucrose | 1 |
| Meat extract | 5 |
| Protein hydrolysate | 2.5 |
| Chicken powder | 3 |
| Chicken fat | 5 |
| Pieces dry chicken | 2 |
| Noodles | 30 |
| Dried parsley | 0,3 |
| Mixed spices | 2 |

This mixture was used for preparing approximately one liter of chicken soup by boiling it with one liter of water for 10 minutes.

The soup thus obtained was divided into two portions. To the first portion 2 ml of the flavouring mixture prepared according to Example A1 were added. Both soups were compared by a panel consisting of 12 persons of which the majority preferred the soup flavoured according to the invention.

EXAMPLE D8

A gravy was prepared from the following ingredients:

| | grams |
|---|---|
| Potato starch | 15 |
| Onion powder | 2.5 |
| Monosodium glutamate | 3 |
| Beef tallow | 20 |
| Flour | 15 |
| Caramel | 1.6 |
| Pepper | 0.02 |
| Bayleaves | 0.02 |
| Clove | 0.02 |
| Sodium chloride | 8 |
| Protein hydrolysate | 4 |
| Beef extract powder | 2 |
| Tomato powder | 1 |
| | 72.16 |

The potato starch and flour were added to the molten beef tallow at 60° C. under continuous stirring. The other ingredients were well blended and likewise added to the beef tallow. The whole mixture was boiled in 1 liter of water.

The gravy so obtained was divided into two portions of 500 ml. In the first portion 250 mg of malto-dextrin was dissolved; in the second portion 250 mg of the flavour powder prepared according to Example C8. Both gravies were assessed in a paired comparison test by a panel consisting of 12 persons.

The gravy containing the flavour powder was preferred by 10 out of the 12 tasters because of its more pronounced fried-meat flavour.

EXAMPLE D9

A basic composition for a dry beef soup was obtained by mixing the following ingredients:

| | grams |
|---|---|
| Onion powder | 0.5 |
| Spice mix | 0.5 |
| Fat | 4 |
| Dried soup vegetables | 1 |
| Monosodium glutamate | 2 |
| Modified potato starch | 3 |
| Noodles | 20 |
| Salt | 8 |

One liter of water was added to the mixture and the whole was boiled for 5 minutes. The soup so obtained was divided in two portions of 500 ml. In the first portion 150 mg of malto-dextrin was dissolved and in the section portion 150 mg of the flavour powder prepared according to example C8.

Both soups were assessed in a paired comparison test by a panel consisting of 8 persons. The soup containing the flavour powder had a characteristic beef flavour and was preferred by 7 out of the 8 testers.

EXAMPLE D10

1 liter gravy was prepared according to the method described in Example D8. This gravy was divided into two portions of 500 ml each. To the first portion 125 mg of malto-dextrin was added and to the second portion 125 mg of the flavour powder prepared according to Example C9. Subsequently both gravies were boiled for 5 minutes and judged afterwards by a panel consisting of 9 expert tasters. Of these, 7 persons preferred the gravy with the aroma powder, while the other 2 expressed no preference. A fuller flavour and a more meaty taste were given as reasons for the preference.

EXAMPLE D11

100 g of textured vegetable protein (T.V.P.) was boiled for 15 minutes in 500 ml of water together with:

|  | grams |
|---|---|
| Monosodium glutamate | 1.85 |
| Salt | 4.0 |
| Protein hydrolysate | 1.1 |
| Spices | 0.45 |
| Flavour powder prepared According to Example C 9 | 6.0 |

The T.V.P. thus obtained was compared with the product in which the flavour powder was replaced by 6.0 g of malto-dextrin. Both T.V.P. products were assessed in a paired comparison test. The product with the flavour powder was generally preferred. A fuller flavour and a more pronounced meaty taste were given as reasons for this preference.

EXAMPLE D12

Minced meat was prepared from the following ingredients:

|  | grams |
|---|---|
| Sausage meat | 825 |
| Salt | 10 |
| Whole egg | 82.5 |
| Bread-crumbs | 82.5 |
|  | 1000 |

The minced meat so obtained was divided into two portions of 500 g each. To the first portion was added a mixture of 10 g of bread-crumbs and 0.25 g malto-dextrin, and to the second portion a mixture of 10 g of bread-crumbs and 0.25 g of the flavour powder prepared according to Example C10. Meat balls prepared from each portion were fried in margarine for 30 minutes. The meat balls of both portions were assessed in a paired comparison test by a panel consisting of 8 persons. An unanimous preference was shown for the meat balls containing the flavour powder, because of the more pronounced fried-meat flavour.

EXAMPLE D13

A basis for canned beef soup was prepared by adding the following ingredients to 4 liters of water:

|  | grams |
|---|---|
| Noodles | 160 |
| Herbs and spices | 1.6 |
| Tallow | 80 |
| Vegetables | 400 |
| Monosodium glutamate | 16 |
| Protein hydrolysate | 16 |
| Meat extract | 16 |
| Salt | 64 |
| Raw meat | 400 |

The total amount was divided into two portions, each of 2 liters. 1.4 g of the flavoured solution prepared according to Example C11 was added to one of the portions. The second portion which was used without further addition, served as a control. The mixtures thus obtained were canned in half liter tins and sterilised in an autoclave. A soup ready for consumption was prepared by adding an eqaul volume of water to the contents of each tin. After heating, both soups were served to a panel consisting of 19 persons for organoleptic testing. The soup with the flavour solution was preferred by 15 persons, because of its more pronounced meaty flavor.

EXAMPLE D14

One liter of gravy was prepared according to the method described in Example D8. This gravy was divided into two portions of 500 ml each. To one of the portions was added 0.2 g of the flavoured solution obtained in Example C11, while the other portion was used without further addition. Both gravies were judged by a panel consisting of 9 persons. Of these panel 8 persons preferred the gravy with the flavour solution. A more pronounced meaty taste and a fuller flavour were given as reasons for the preference.

EXAMPLE D15

One liter of gravy was prepared according to the method described in Example D8. This gravy was divided into two portions of 500 ml each. To the first portion was added 0.5 g of the flavoured solution prepared according to Example C13, and to the second portion, 0.5 g of a solution prepared according to the method described in Example C13, except that the 1 g of 4-hydroxy-2,3-dihydrofuran-3-one had been omitted. Both gravies were assessed in a paired comparison test by a panel consisting of 9 persons. The gravy portion containing the flavoured solution prepared, using all the ingredients of Example C12, was significantly preferred because of its more pronounced meat flavour.

EXAMPLE D16

One liter of gravy was prepared according to the method described in Example D8. The gravy was divided into two portions of 500 ml each. To the first portion was added 250 mg of the flavour powder prepared according to the method described in Example C8, and to the second portion was added 12.5 mg of 4-hydroxy-5-methyl-2,3-dihydrofuran-3-one. Both gravies were assessed in a paired comparison test by a panel consisting of 16 expert tasters. The gravy containing the flavour powder was preferred by 12 out of 16 persons because of its more pronounced fried-meat flavour.

EXAMPLE D17

A mixture of 1.0 g of 4-acetoxy-5-methyl-2,3-dihydrofuran-3-one, 2.0 g of thioacetamide and 20 ml of water were heated together in a round bottomed flask at 100° C for 4 hours. The reaction mixture was then allowed to cool. It had a good roast-beef flavour and was considered a favourable additive to a beef soup prepared according to Example D9.

What is claimed is:

1. A compound of the general formula

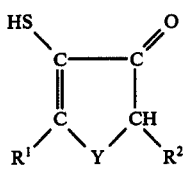

in which Y represents an oxygen and $R^1$ and $R^2$ represent a hydrogen or an alkyl or hydroxyalkyl group containing together from 1 – 9 carbon atoms.

2. A compound of the general formula

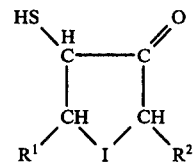

in which Y represents an oxygen and $R^1$ and $R^2$ represent a hydrogen or an alkyl or hydroxyalkyl group containing together from 1 – 9 carbon atoms.

3. A compound according to claim 1, in which $R^1$ and $R^2$ represent a hydrogen atom, a methyl group or a hydroxymethyl group.

* * * * *

UNITED STATES PATENT AND TRADEMARK OFFICE
CERTIFICATE OF CORRECTION

PATENT NO. : 4,080,367
DATED : March 21, 1978
INVENTOR(S) : Van den Ouweland et al It is certified that error appears in the above-identified patent and that said Letters Patent are hereby corrected as shown below:

In the Claims:

Claim 2, column 34, lines 3-8:

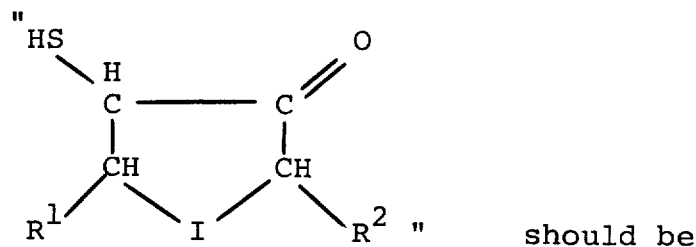

should be

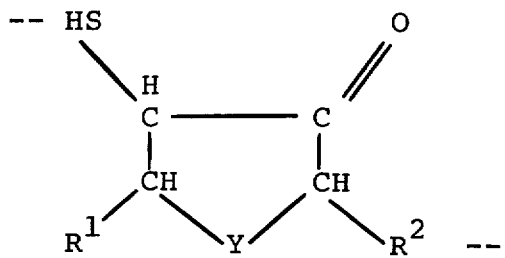

Signed and Sealed this

Seventeenth Day of October 1978

[SEAL]

Attest:

RUTH C. MASON
Attesting Officer

DONALD W. BANNER
Commissioner of Patents and Trademarks